(12) United States Patent
Elsoee et al.

(10) Patent No.: US 9,854,817 B2
(45) Date of Patent: Jan. 2, 2018

(54) MEAT PROCESSING DEVICE INCORPORATING AN X-RAY ANALYZER

(71) Applicant: Foss Analytical A/S, Hilleroed (DK)

(72) Inventors: Maja Kirstine Elsoee, Birkeroed (DK); Hans Larsen, Hoersholm (DK); Stefan Linn, Runkel (DE); Allan Kjaergaard Jensen, Vanloese (DK)

(73) Assignee: Foss Analytical A/S, Hilleroed (DK)

( * ) Notice: Subject to any disclaimer, the term of this patent is extended or adjusted under 35 U.S.C. 154(b) by 62 days.

(21) Appl. No.: 14/890,580

(22) PCT Filed: Jul. 11, 2013

(86) PCT No.: PCT/EP2013/064712
§ 371 (c)(1),
(2) Date: Nov. 11, 2015

(87) PCT Pub. No.: WO2015/003750
PCT Pub. Date: Jan. 15, 2015

(65) Prior Publication Data
US 2016/0081360 A1 Mar. 24, 2016

(51) Int. Cl.
| | | |
|---|---|---|
| H05K 7/20 | (2006.01) | |
| B02C 18/30 | (2006.01) | |
| A22C 17/00 | (2006.01) | |
| G01N 33/12 | (2006.01) | |
| G01N 23/083 | (2006.01) | |

(52) U.S. Cl.
CPC ........ *A22C 17/0073* (2013.01); *A22C 17/008* (2013.01); *G01N 23/083* (2013.01); *G01N 33/12* (2013.01); *G01N 2223/618* (2013.01); *G01N 2223/643* (2013.01); *G01N 2223/652* (2013.01)

(58) Field of Classification Search
CPC .. G01N 23/046; G01N 223/419; G01N 23/18; G01N 2223/646
USPC .......................... 378/57, 210, 68, 69; 165/47
See application file for complete search history.

(56) References Cited

U.S. PATENT DOCUMENTS

| | | | | |
|---|---|---|---|---|
| 4,141,164 | A | 2/1979 | Hillberg | |
| 7,607,597 | B2 * | 10/2009 | Linn ........................ | A22C 5/00 241/101.2 |
| 2005/0287252 | A1 | 12/2005 | Schrock et al. | |
| 2008/0286424 | A1 * | 11/2008 | Patel ........................ | A23C 3/07 426/240 |

(Continued)

FOREIGN PATENT DOCUMENTS

WO  WO-2013023778 A1   2/2013

OTHER PUBLICATIONS

International Search Report PCT/ISA/210 for International Application No. PCT/EP2013/064712 dated Mar. 27, 2014.

(Continued)

*Primary Examiner* — Don Wong
(74) *Attorney, Agent, or Firm* — Harness, Dickey & Pierce

(57) ABSTRACT

A meat processing device comprises a meat processing unit and an external X-ray meat analyzer provided with a housing formed with an inlet connectable with an outlet of the processing unit. The housing provides complete shielding of personnel from X-rays except towards the inlet and is movable relative to the processing unit to a first position for analysis at which the unit outlet is collocated with the inlet and at which the processing unit completes the shielding of personnel from X-rays towards the inlet.

11 Claims, 3 Drawing Sheets

(56) References Cited

U.S. PATENT DOCUMENTS

| | | | | |
|---|---|---|---|---|
| 2011/0058650 A1* | 3/2011 | Makino | ............... | G01V 5/00 |
| | | | | 378/57 |
| 2012/0307013 A1* | 12/2012 | Hjalmarsson | ...... | A22C 17/0086 |
| | | | | 348/46 |

OTHER PUBLICATIONS

Written Opinion of the International Searching Authority PCT/ISA/237 for International Application No. PCT/EP2013/064712 dated Mar. 27, 2014.

* cited by examiner

MEAT PROCESSING DEVICE INCORPORATING AN X-RAY ANALYZER

CROSS-REFERENCE TO RELATED APPLICATIONS

This application is a national phase under 35 U.S.C. §371 of PCT International Application No. PCT/EP2013/064712 which has an International filing date of Jul. 11, 2013 the entire contents of each of which are hereby incorporated herein by reference.

The present invention relates to a meat processing device for the processing of fresh and/or frozen meat and meat products and in particular to a device which has incorporated an X-ray analyzer for determining compositional properties, such as fat content, contamination or foreign object inclusion, of the processed meat or meat product.

The compositional analysis of meat and meat products (hereinafter generally referred to as 'meat') by means of X-ray has been known for many years and was reported as early as 1997 (Meat Science Vol. 47, No 1-2, 115-124—A. D. Mitchell, M. B. Solomon & T. S. Rumsey). A method and a system for the analysis of meat, particularly the fat content of meat, in a production line is described in U.S. Pat. No. 6,600,805 (Hansen) and involves the use of a dual energy X-ray analyzer. The system comprises a conveyor belt for receiving meat in an open box and an X-ray arrangement for the transmission and subsequent detection of X-rays having been transmitted through the meat in the box as it is moved by the conveyor belt. The so disclosed system is a stand-alone system intended for insertion at any suitable location within the production line. However, being stand-alone, the system must have complete X-ray shielding to prevent irradiation of personnel. This adds significantly to the cost and makes the system rather large and heavy.

A meat processing device is disclosed in U.S. Pat. No. 7,607,597 (Linn et al.) and comprises a meat processing unit, such as a unit for mincing, filling, degassing and or mixing fresh or frozen meat or meat product and associated therewith an X-ray based fat analyzer. A device is described in which the X-ray source and the complementary detector of the X-ray analyzer are mounted on and are intended to form a part of the processing unit, such as on an outlet pipe in the vicinity of a screw conveyor for conveying the processed meat out of the unit, and are arranged for illumination of processed meat at an analysis zone internal the processing unit in a direction substantially perpendicular to the direction of conveyance of the meat. However in this arrangement analysis must be performed in a timed relationship with the rotation of the screw conveyor or must be made at the periphery of the conveyed processed meat so as to avoid the 'threads' of screw conveyor interrupting the X-ray beam during measurements. External protective shielding at the output of the meat processing unit is still necessary in order to prevent an operator's accidental physical engagement with dangerous moving parts, for example the output screw conveyor, within the unit.

It is an aim of the present invention to at least mitigate one of the aforementioned problems associated with the known meat processing device and/or X-ray analyzer for meat.

Accordingly there is provided a meat processing device comprising a meat processing unit for processing meat or meat product, the unit having a unit outlet; and an X-ray analyzer having an X-ray source for emitting X-rays towards the processed meat at an analysis zone and an associated X-ray detector for detecting X-rays from the source having interacted with the processed meat wherein the X-ray analyzer comprises a housing having an inlet to and an outlet from internal the housing and being constructed to provide complete shielding for personnel from X-rays except towards the inlet; a conveyor for conveying processed meat from the inlet to the outlet internal the housing, through the analysis zone external of the processing unit; the X-ray source and the X-ray detector being disposed internal the housing to analyze processed meat on the conveyor; and wherein the housing is disposed external the processing unit such that the inlet cooperates with the unit outlet to provide an enclosed passageway for processed meat from internal the processing unit to internal the housing and to complete the shielding of personnel from X-rays towards the inlet. Thus by arranging for the X-ray shielding to be completed by the processing unit then the amount of shielding required on the housing may be reduced. Moreover, since an enclosed passageway is formed between the processing unit and the housing then the external protective shielding on the processing unit to prevent accidental access to internal that unit may be avoided. In an embodiment the unit outlet may be configured to project through the inlet and into the housing, preferably avoiding impinging the analysis zone, thereby ensuring a safer shielding from X-rays and also from access to internal the meat processing unit.

In one embodiment the X-ray analyzer is made movable relative to the meat processing unit to and from a first position at which the unit outlet and the inlet are collocated to form the enclosed passageway. Usefully the X-ray analyzer and the meat processing unit are hingedly connected for rotation of the analyzer about the hinge to and from the first position. Thus the relative movement is controlled which facilitates the accurate and repeatable movement of the X-ray analyzer to and from the first position.

In another embodiment, which may be combined with or taken separately from other embodiments, there is provided an interlock which may be mechanical, electronic or a combination of the two and which is adapted to prevent the operation of one or both the processing unit and the X-ray analyzer until the analyzer is moved to the first position and thus helps prevent accidental access to internal the meat processing device whilst it is in operation.

These, as well as additional objects, features and advantages of the present invention, will be better understood through the following illustrative and non-limiting detailed description of embodiments of the present invention, made with reference to the drawings of the appended figures, of which:

Figure 1:
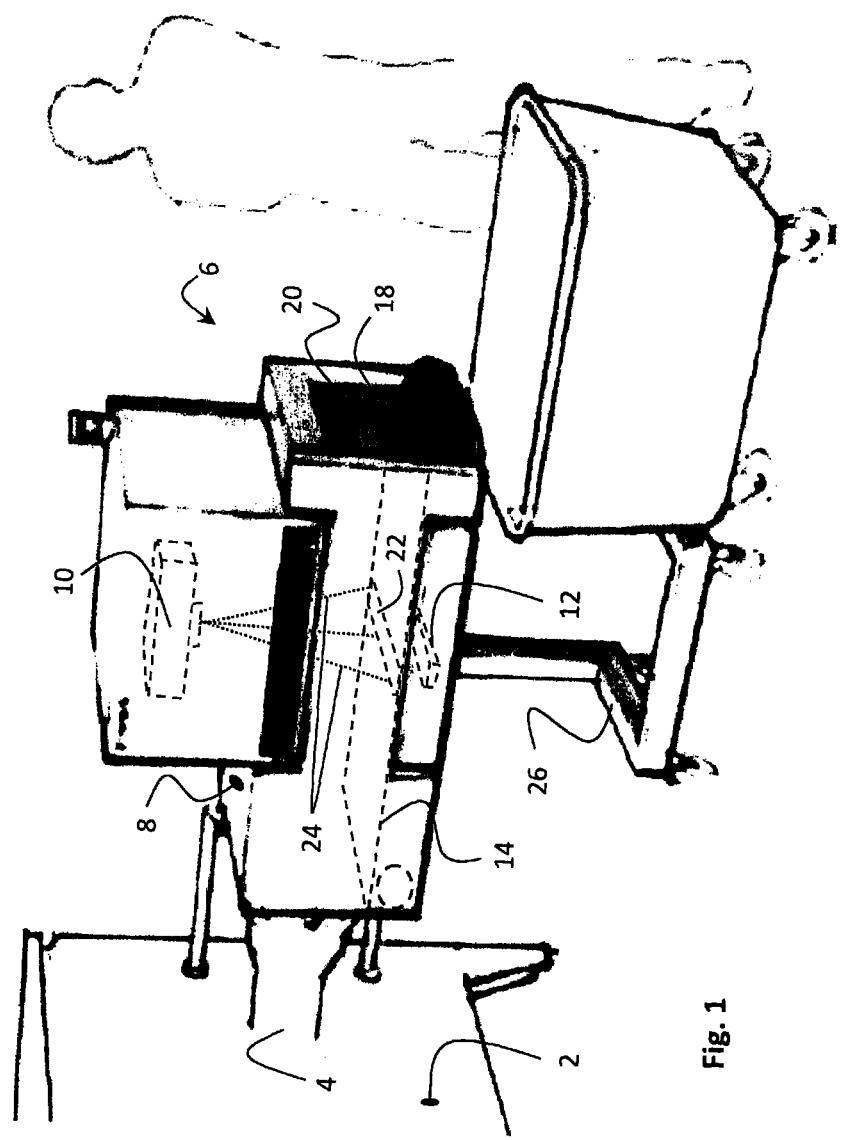
FIG. 1 shows an embodiment of a device according to the present invention where the x-ray analyzer is in a first position.

An exemplary embodiment of the present invention will now be described with reference to the drawings of FIGS. 1 to 3. A meat processing device is illustrated which comprises a meat processing unit 2, such as a unit for mincing, filling, degassing and/or mixing fresh and/or frozen meat and/or meat product, said unit 2 having a unit outlet 4; and an X-ray analyzer 6 disposed external the meat processing unit 2. The X-ray analyzer 6 comprises a housing 8 within which is located an X-ray source 10; a complementary X-ray detector 12 and a conveyor 14.

The housing 8 is formed with an inlet 16 and an outlet 18 between which the conveyor 14 is disposed to convey processed meat passing from the outlet 4 of the meat processing unit 2 through an analysis zone 22 internal of the housing 8 and thus external of the processing unit 2. The analysis zone 22 is delimited by the region of an X-ray beam (here a fan shaped beam) 24 emitted by the source 10 as it intersects the conveyor 14 inside the housing 8. The X-ray detector 12 is disposed relative to the analysis zone 22 so as to detect X-ray having passed through meat in the analysis zone 22. In the present embodiment the X-ray source 10 is located above the conveyor 14 and the detector 12 below the conveyor 14 which is formed of an X-ray transparent material, at least in the region intersected by the X-ray beam 24. A signal processor (not shown) is operably connectable with the output of the detector 12 to receive signals therefrom representative of the intensities of X-rays incident at the detector and to process these signals in a known manner to provide a compositional analysis (such as fat content or presence of contamination or foreign objects) of the meat in the analysis zone 24.

The housing 8 itself is constructed to provide complete shielding of personnel from X-rays emitted by the X-ray source 10 except towards the inlet 16, i.e the housing 8 is provided with a relatively reduced X-ray shielding capacity in a region towards its inlet 16. In the present embodiment X-ray curtains 20 are provided at the outlet 18 of the housing 8 to contribute to the shielding of the personnel but no similar shielding is provided at the inlet 16. The lack of X-ray curtains at the inlet 16 provides an advantage for the device according to the present example since there is no risk of such curtains being moved internal the housing to impinge and shadow meat in the analysis zone as other meat is conveyed through the inlet 16.

Figure 2:
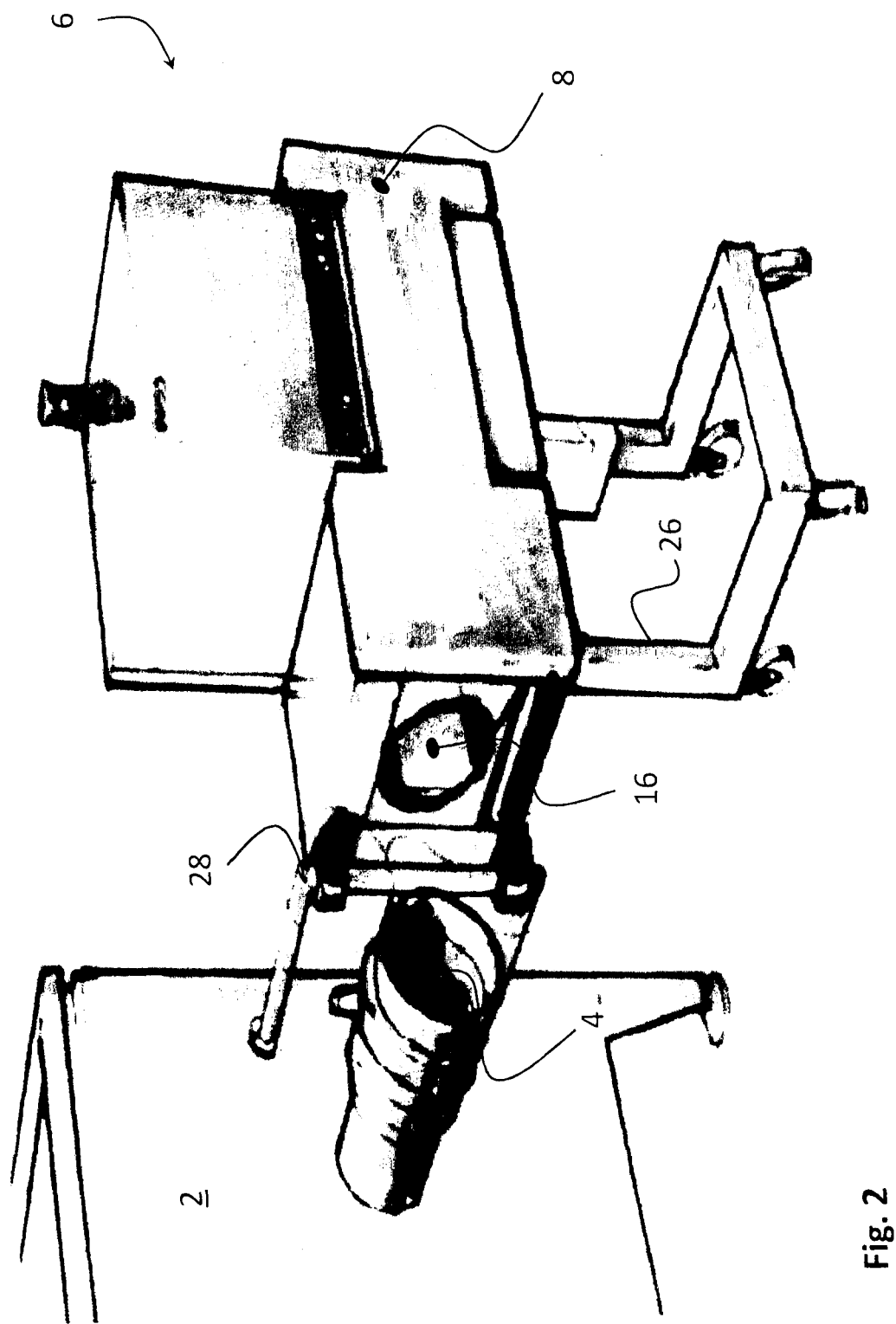
FIG. 2 shows the device of FIG. 1 where the x-ray analyzer is in a second position.
Figure 3:
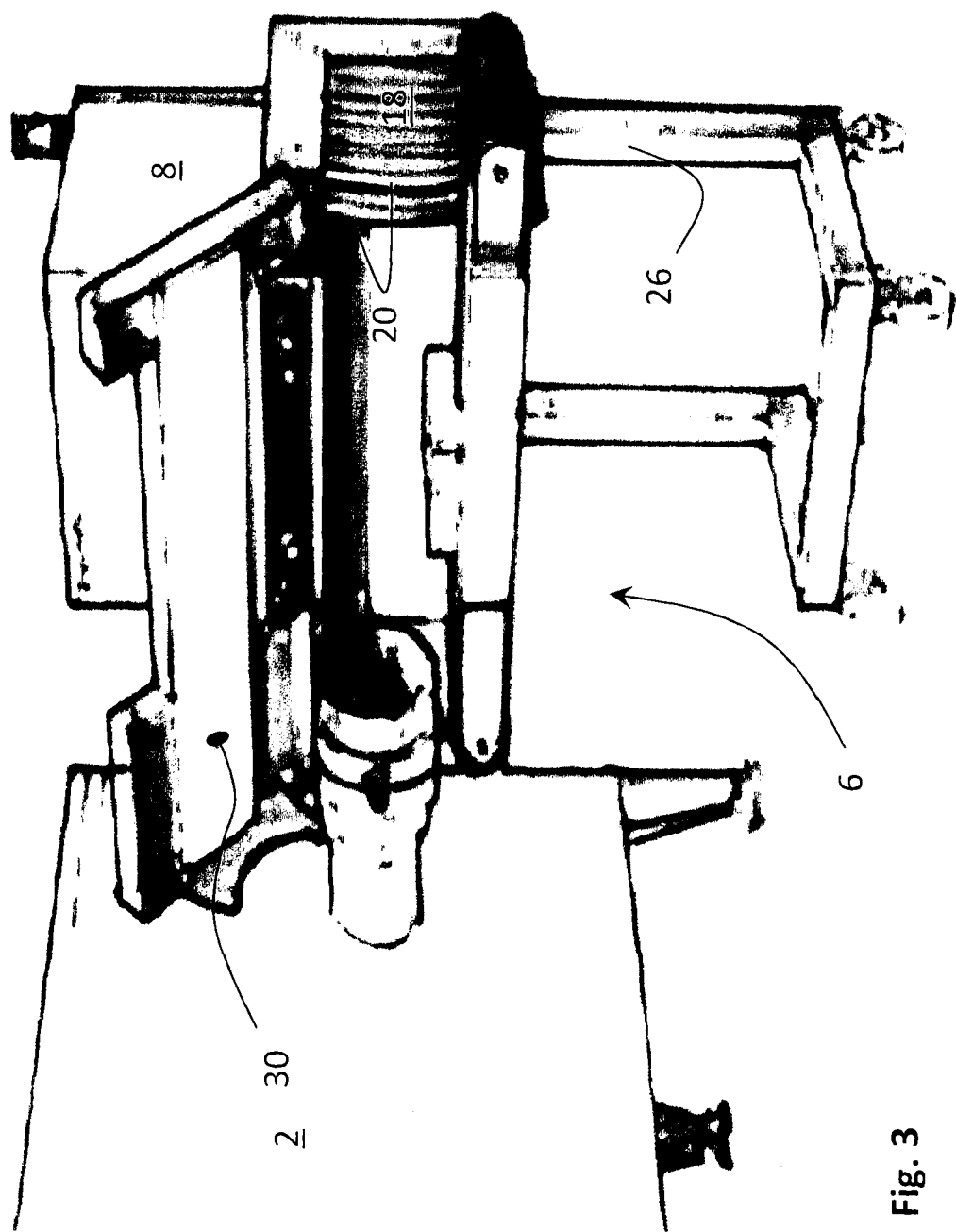
FIG. 3 shows the device according to FIG. 1 opened to expose internal the analyzer housing.

In the present embodiment an entirely optional wheeled support 26 is provided for the X-ray analyzer 6 to facilitate its movement relative to the meat processing unit 2 between a first position (illustrated in FIG. 1) and a second position (illustrated in FIG. 2). In the first position the outlet 4 of the meat processing unit 2 is collocated with the inlet 16 of the X-ray analyzer 6 (here in this embodiment projects past the inlet 16, see FIG. 3) to provide an enclosed passageway for processed meat from the unit 2 to internal the housing 8 and to complete the shielding of personnel from X-rays towards the inlet 16. In this first position analysis of the processed meat is possible. As a complement to this, in this first position the housing 8 provides a safety shielding which prevents access by personnel to internal the meat processing unit 2 via its otherwise open outlet 4. In this manner shielding which would necessarily need to be provided for each of the meat processing unit 2 and the X-ray analyzer 6 is avoided, or at least shared between the two elements 2, 6. In the second position the inlet 16 of X-ray analyzer 6 is disengaged from the outlet 4 of the meat processing unit 2. In this second position no analysis may be safely performed and preferably the processing unit 2 should not be operated.

According to the present embodiment and independent of the other features of this embodiment a hinge assembly 28 may be provided to couple together the processing unit 2 and the analyzer 6 and provide for a rotational movement of the analyzer 6 between the first and the second positions in a repeatable manner. In this way the movement of the analyzer 6 is guided to ensure proper collocation of the outlet 4 and inlet 16 and thereby safe operation of the meat processing device.

Again, according to the present embodiment and independent of the other features of this embodiment the housing 8 of the X-ray analyzer 6 may be provided with a hinged body section 30 (see FIG. 3) which may be moved about the hinge to expose the internal of the housing 8. This may be advantageous when cleaning the analyzer 6 or when performing service or repair.

The meat processing device according to the present invention may be provided with a mechanical or electronic interlock (not shown) of generally known construction and which is configured to prevent the operation of one or both of the meat processing unit 2 and the X-ray analyzer 6 until the analyzer 6 is positioned in the first position (see the associated description made with reference to FIG. 1). The interlock may be adapted to prevent the operation of only the processing unit 2. Additionally or alternatively the interlock may be adapted to prevent movement of the X-ray analyzer 6 whilst the processing unit 2 is operating or may be adapted to prevent movement of the hinged body portion 30 (when provided) of the X-ray analyzer 6 whilst the processing unit 2 is operating, thereby inhibiting a user's access to internal the processing unit 2 and any moving parts thereof.

The invention claimed is:

1. A meat processing device comprising:
   a meat processing unit configured to process meat or meat product to form processed meat, the meat processing unit including an outlet; and
   an X-ray analyzer including,
      an X-ray source configured to emit an X-ray beam towards the processed meat in the X-ray analyzer,
      an X-ray detector configured to detect X-rays from the X-ray source having interacted with the processed meat,
      a housing including an inlet configured to selectively couple with the outlet of the meat processing unit to form an enclosed passageway therebetween such that the housing allows the X-rays to radiate outside the housing only through the inlet,
      X-ray curtains located only over the outlet, the X-ray curtains configured to prevent radiation of X-rays outside of the housing through the outlet, and
      a conveyor located internal to the housing and configured to convey the processed meat from the inlet-through the housing, a portion of the conveyor being vertically aligned with the outlet when the housing is coupled to the meat processing unit such that the processed meat that is output from the outlet falls onto the conveyor,
   wherein the X-ray analyzer is movable relative to the meat processing unit such that the X-ray analyzer moves to and from a first position at which the outlet and the inlet are collocated such that the outlet is configured to couple with the inlet to form the enclosed passageway,
   wherein the outlet of the meat processing unit is configured to project past the inlet of the housing and into the housing at a distance such that the outlet does not impinge on an analysis zone in the X-ray analyzer, based on the X-ray analyzer being at the first position.

2. The meat processing device of claim 1, wherein the X-ray analyzer and the meat processing unit are hingedly connected such that the X-ray analyzer rotates about a hinge to and from the first position.

3. The meat processing device of claim 1, further comprising:
   an interlock configured to prevent operation of at least one of the meat processing unit and the X-ray analyzer until the X-ray analyzer is moved to the first position.

4. The meat processing device of claim 3, wherein the interlock is configured to prevent the operation of the meat processing unit.

5. The meat processing device of claim 3, wherein the interlock is configured to prevent a movement of the X-ray analyzer, if the meat processing unit is operating.

6. The meat processing device of claim 3, wherein the housing includes a hinged body portion configured to open to expose internal of the housing, and the interlock is configured to prevent an opening of the hinged body portion, if the meat processing unit is operating.

7. A meat analysis device comprising:

a housing including an inlet, an outlet, and a coupler including a hinge configured to rotate the meat analysis device between a first position and a second position relative to a meat processor, so that in the first position the inlet of the housing is coupled with an outlet of the meat processor to form an enclosed passage between the meat analysis device and the meat processor such that the housing receives processed meat while shielding personnel from radiation emitted by the meat analysis device;

an X-ray radiation source within the housing, the X-ray radiation source configured to emit X-ray radiation towards the processed meat in the housing;

X-ray curtains located only over the outlet, the X-ray curtains configured to prevent radiation of X-rays outside of the housing through the outlet;

a radiation detector within the housing, the radiation detector configured to detect radiation from the X-ray radiation source that penetrates the processed meat; and a transfer device within the housing, the transfer device including a conveyor, a portion of the conveyor being vertically aligned with the outlet of the meat processor when the housing is coupled to the meat processor such that the processed meat is output from the outlet falls onto the conveyor to be conveyed to the outlet of the housing.

8. The meat analysis device of claim 7, wherein the transfer device is between the X-ray radiation source and the radiation detector.

9. The meat analysis device of claim 8, wherein the meat analysis device is configured to couple with the meat processor to form the enclosed passage, if the meat analysis device is at the first position.

10. The meat analysis device of claim 9, wherein the outlet of the meat processor includes a first portion and a second portion separated by a band, a diameter of the band being larger than a diameter of the inlet, the second portion being tapered towards end thereof and configured to penetrate the housing via the inlet.

11. The meat analysis device of claim 10, wherein, if the meat analysis device is at the first position, a path from the X-ray radiation source to the processed meat on the conveyor is unobstructed by the second portion of the outlet.

* * * * *